(12) United States Patent
Johnson

(10) Patent No.: US 7,785,582 B2
(45) Date of Patent: Aug. 31, 2010

(54) USE OF SYNOVIUM AND OMENTUM FOR TISSUE ENGINEERING

(76) Inventor: Lanny L. Johnson, 4658 Chippewa Dr., Okemos, MI (US) 48864

( * ) Notice: Subject to any disclaimer, the term of this patent is extended or adjusted under 35 U.S.C. 154(b) by 0 days.

(21) Appl. No.: 11/210,077

(22) Filed: Aug. 23, 2005

(65) Prior Publication Data

US 2006/0051327 A1 Mar. 9, 2006

Related U.S. Application Data

(60) Provisional application No. 60/622,446, filed on Oct. 27, 2004, provisional application No. 60/607,676, filed on Sep. 7, 2004.

(51) Int. Cl.
*A01N 65/00* (2006.01)

(52) U.S. Cl. .................. 424/93.7; 514/12; 435/366

(58) Field of Classification Search ................ 424/93.7
See application file for complete search history.

(56) References Cited

U.S. PATENT DOCUMENTS

| | | | |
|---|---|---|---|
| 5,004,681 | A | 4/1991 | Boyse et al. |
| 5,192,553 | A | 3/1993 | Boyse et al. |
| 5,197,985 | A | 3/1993 | Caplan et al. |
| 5,226,914 | A | 7/1993 | Caplan et al. |
| 5,811,094 | A | 9/1998 | Caplan et al. |
| 5,842,477 | A | 12/1998 | Naughton et al. |
| 5,908,784 | A | 6/1999 | Johnstone et al. |
| 6,080,194 | A | 6/2000 | Pachence et al. |
| 6,174,333 | B1 | 1/2001 | Kadiyala et al. |
| 6,387,369 | B1 | 5/2002 | Pittenger et al. |
| 6,461,645 | B1 | 10/2002 | Boyse et al. |
| 6,569,427 | B1 | 5/2003 | Boyse et al. |
| 6,602,294 | B1 | 8/2003 | Sittinger et al. |
| 6,605,275 | B1 | 8/2003 | Boyse et al. |
| 2002/0122790 | A1 | 9/2002 | Hunziker |
| 2003/0130250 | A1 | 7/2003 | Bridger et al. |
| 2004/0028717 | A1 | 2/2004 | Sittinger et al. |

OTHER PUBLICATIONS

Luyten et al, Best Practice and Research Clinical Rheumatology, vol. 15, 2001, p. 759-769.*
Collins et al, Clinical and Diagnostic laboratory immunology, vol. 3, 1996, p. 5-9.*
Nishimura et al, Arthritis and Rheumatism , vol. 42, 1999, p. 2631-2637.*
Hunziker et al., Repair of Partial-Thickness Defects in Articular Cartilage: Cell Recruitment from the Synovial Membrane, J. Bone Joint Surg. Am. May 1996; 78(5) 721-33.
Hunziker et al., Repair of Partial-Thickness Defects in Articular Cartilage: Cell Recruitment from the Synovial Membrane, J. Bone Joint Surg. Am. May 1996, Abstract.
Rovensky et al., Hormone concentrations in synovial fluid of patients with rheumatoid arthritis, Clin Exp Rheumatol. May-Jun. 2005, Abstract.
Sakaguchi et al., Comparison of human stem cells derived from various mesenchymal tissues: superiority of synovium as a cell source, Arthritis Rheum. Aug. 2005, Abstract.
Johnson, Lanny, Unpublished document.
De Bari et al., Arthritis Rheum. Aug. 2001; 44(8): 1928-42.
Vandenabeele et al. Arch Histol Cytol. May 2003; 66(2): 145-53.
De Bari et al., Journal of Cell Biology 160:6 909-918 (2003).
De Bari et al., Arthritis & Rheumatism vol. 50 No. 1, pp. 142-150.
Key, J. Albert, The reformation of synovial membrane in the knees of rabbits after synovectomy. J. Bone Joint Surg. 7:793. 1925.
Quesenberry and Becker, Proc. Natl. Acad. Sci. USA, vol. 95, pp. 15155-15157 (1998).
Scheffold et al., Purified allogeneic hematopoietic stem cell transplantation prevents autoimmune diabetes and induces tolerance to donor matched islets. Blood. 1999;94 (suppl 1): 664a.
Perry T.E. and Roth S.J., Cardiovascular tissue engineering: constructing living tissue cardiac valves and blood vessels using bone marrow, umbilical cord blood, and peripheral blood cells. J. Cardiovasc Nurs. 2003;18:30-37.
Kowalczyk et al., Omentum major as potential source of osteogenic cells for tissue engineering (preliminary report). 2003;07-21; 13:17.

* cited by examiner

*Primary Examiner*—Jon P Weber
*Assistant Examiner*—Tiffany M Gough
(74) *Attorney, Agent, or Firm*—Biotech Beach Law Group PC; Raymond Wagenknecht

(57) ABSTRACT

A method for treating a patient to repair or regenerate damaged tissues or organs in which synovium from a joint or omentum from the abdomen are harvested to provide explants, optionally separating cells from the synovium or omentum explants for culture or tissue specification, and introducting the explants or separated cells from the synovium or omentum into damaged tissues or organs to repair the damaged tissues or organs.

9 Claims, No Drawings

USE OF SYNOVIUM AND OMENTUM FOR TISSUE ENGINEERING

CROSS-REFERENCE TO RELATED APPLICATIONS

This application claims priority to Provisional Application Ser. No. 60/622,446 filed Oct. 27, 2004. This application also claims priority to U.S. Provisional Patent Application Ser. No. 60/607,676 filed Sep. 7, 2004.

STATEMENT REGARDING FEDERALLY SPONSORED RESEARCH OR DEVELOPMENT

Not Applicable

BACKGROUND OF THE INVENTION (1) Field of the Invention

The present invention relates generally to harvesting of synovial villi from a joint and introducing explants or separated cells from the synovium into damaged tissues to repair the injured tissues. Specifically, the present invention relates to repairing tissues or organs such as a joint or elsewhere. The present invention also relates to harvesting omentum from the abdomen and introducing explants or separated cells from the omentum into damaged tissues to repair the injured tissues or organs in the abdomen or elsewhere.

(2) Description of the Related Art

Hematopoietic stem cells (HSCs) are cells which are capable of dividing and differentiating into any cell type of the blood. Two types of HSCs are known to exist: long-term and short-term HSCs. Long-term HSCs cell cycle and divide each day, while short-term HSCs differentiate into lymphoid and myeloid precursors. The lymphoid precursors give rise to T cells, B cells and natural killer cells. The myeloid precursors give rise to monocytes, macrophages, neutrophils, eosinophils, basophils, megakaryocytes, and erythrocytes. Hematopoietic stem and progenitor cells harvested for transplantation have typically come from bone marrow. Recently however, peripheral blood and umbilical cord blood have been used as a source for these cells. Peripheral blood stem cells (PBSC) have been mobilized by various techniques, since stem and progenitor cells are a very low percentage of the cells found in peripheral blood. An apheresis device is used to collect from a patient and automatically separate specific cells from whole blood. Afterwards the remaining blood components are returned to the patient, typically using a dual lumen catheter. Plasma, red blood cells, platelets, and white blood cells can be specifically removed by centrifugation in continuous mode while the remaining blood components are returned to the patient. Blood components which can be separated include plasma (plasmapheresis), platelets (plateletpheresis), and leukocytes (leukapheresis). Apheresis can be used to separate mononuclear cells (MNC) which include stem cells.

The stem and progenitor cells in peripheral blood can be increased prior to apheresis by myelosuppressive chemotherapy mobilization techniques and other drugs. Various myelosuppressive regimens are available including cyclophosphamide. Unfortunately, using such chemotherapy to mobilize PBSC can have an associated risk of toxicity. Since not every patient who must receive stem and progenitor cells will require chemotherapy for an associated illness, this is not always an appropriate option for mobilizing stem and progenitor cells from bone marrow. Recent approaches to mobilizing stem and progenitor cells utilize hematopoietic growth factors. Such growth factor mobilization procedures use filgrastim (granulocyte colony-stimulating factor [G-CSF]), sargramostim (granulocyte-macrophage colony-stimulating factor [GM-CSF]), or combinations thereof. G-CSF is administered subcutaneously at a dose of 10 to 16 micrograms per day (μg/d), which typically results in a peak level of circulating progenitor cells at day 4 to 7 after starting G-CSF administration. Other growth factors such as stem cell factor (SCF) can also be used to mobilize stem cells into the peripheral blood. Stress, injury, estrogen therapy, physical training, and nanopulses have all been shown to mobilize cells progenitor and stem cells in the peripheral blood.

Alternatively, stem cells can be isolated from adult human synovial membrane as described by De Bari et al. *Arthritis Rheum.* 2001 August; 44(8):1928-42. Cultured fibroblast-like cells derived from adult human synovial membrane have been characterized by Vandenabeele et al. *Arch Histol Cytol.* 2003 May; 66(2):145-53. Skeletal muscle repair by stem cells from synovial membrane was described by De Bari et al. *Journal of Cell Biology* 160:6 909-918 (2003). However, De Bari et al. *Arthritis & Rheumatism* vol 50 no. 1, pp. 142-150 found that in-vitro differentiated stem cells from synovial membrane failed to form ectopic cartilage. Kowalczyk et al. suggests that the omentum major may be another a potential source of osteogenic cells for tissue engineering.

U.S. Pat. No. 6,080,194 to Pachence et al. disclose a porous collagen-based implant for use in the repair of cartilage lesions. U.S. Pat. No. 6,602,294 B1 and U.S. Patent Application Publication No. 2004/0028717 A1 to Sittinger et al. disclose implantable substrates for the healing and protection of connective tissue, preferably cartilage. U.S. Pat. No. 5,842,477 to Naughton et al. teaches methods for repairing cartilage by implanting biocompatible scaffold in combination with periosteal and/or perichodrial tissue to provide a source of chondrocyte progenitor cells, chondrocytes and other stromal cells for attachment to the scaffold.

While the related art teach chemical or hematopoietic growth factor mobilization of stem cells from bone marrow and various implantable substrates for the healing of cartilage, there still exists a need for methods of harvesting stem and progenitor cells from the body which can be introduced into tissues of a patient to repair and regenerate damaged tissue.

OBJECTS

Therefore, it is an object of the present invention to provide a method of treating a patient to regenerate damaged tissue.

It is further an object of the present invention to provide a method of repairing damaged tissues by harvesting cells from synovial villi and introducing cells from the synovial villi into the damaged tissues.

It is further an object of the present invention to provide a method of repairing damaged tissues by harvesting cells from omentum of the abdomen and introducing cells from the omentum into the damaged tissues.

These and other objects will become increasingly apparent by reference to the following description.

SUMMARY OF THE INVENTION

The present invention provides a method for treating a patient to repair damaged tissue which comprises harvesting synovium tissue from a joint, separating synovial cells from the synovium tissue, and introducing the separated cells into the damaged tissue so as to repair the damaged tissue in the presence of the cells. In further embodiments the damaged tissue is articular cartilage. In still further embodiments the synovium tissue is inflamed with villous protrusions from which the synovium is harvested.

The present invention provides a method for treating a patient to repair damaged tissue which comprises harvesting omentum tissue from the patient, separating the cells from the harvested omentum tissue from the patient, and introducing the separated cells into the damaged tissue of the patient so as to repair the damaged tissue.

The present invention provides a method for repairing damaged tissue in a patient which comprises harvesting synovium tissue from a joint or omentum from the abdomen, separating cells from the synovium tissue or omentum, placing the separated cells into a biologically compatible vehicle, culturing the cells within the vehicle in a tissue culture medium, and introducing the cultured cells within the vehicle into the damaged tissue of the patient so as to repair the damaged tissue. In further embodiments the damaged tissue is an organ of the patient. In still further embodiments the separated cells are cultured under conditions which give rise to specific cells of the damaged tissue to be repaired.

The present invention provides a method for providing a store of cells for future use to repair damaged tissue which comprises harvesting synovium tissue or omentum tissue from a patient, separating cells from the harvested tissue of the patient, and freezing the cells separated from the tissue of the patient so as to provide a store of cells from the patient for future use to repair damaged tissues.

The present invention provides a method for treating a patient to repair damaged tissue which comprises harvesting synovium tissue from a joint to provide an explant, and introducing the explant into the damaged tissue so as to repair the damaged tissue in the presence of the cells. In further embodiments the synovium tissue is inflamed with villous protrusions from which the synovium is harvested. In still further embodiments the damaged tissue is articular cartilage.

The present invention provides a method for treating a patient to repair damaged tissue which comprises harvesting omentum tissue from the patient to provide an explant, and introducing the explant into the damaged tissue of the patient so as to repair the damaged tissue.

The present invention provides a method for repairing damaged tissue in a patient which comprises harvesting synovium tissue from a joint or omentum from the abdomen to provide an explant, placing the explant into a biologically compatible vehicle, culturing the explant with the vehicle in a tissue culture medium, and introducing the cultured explant and vehicle into the damaged tissue of the patient so as to repair the damaged tissue. In further embodiments the damaged tissue is an organ of the patient. In still further embodiments the explant is cultured under conditions which give rise to specific cells of the damaged tissue to be repaired.

The present invention provides a cocktail of cells for treating a patient which have been isolated from the body of the patient, the cocktail of cells comprising a population of stem cells, progenitor cells, synovial cells, red blood cells, angioblasts, cartilage cells, white blood cells, fibroblasts, fat cells, or mixtures thereof, wherein the cocktail of cells have been harvested from synovium of a joint. In further embodiments the patient is an animal. In still further embodiments the patient is a human.

The present invention provides a cocktail of cells for treating a patient which have been isolated from the body of the patient, the cocktail of cells comprising a population of stem cells, progenitor cells, flat omentum cells, oval omentum cells, red blood cells, angioblasts, cartilage cells, white blood cells, fibroblasts, fat cells, or mixtures thereof, wherein the cocktail of cells have been harvested from omentum of the abdomen. In further embodiments the patient is an animal. In still further embodiments the patient is a human.

There are three various states of the synovium: normal, injured or diseased, and harvested. The fluids and their contents are also described in the following paragraphs. The post injury or harvest state that may have fibrin clots and eventually more specialized tissue phenotype. The harvested synovial villae is a composite (cocktail) of the various components depending upon whether normal or in state of responding to injury or disease. The same scenario can be formed for omentum.

Normal Synovium: The normal synovium is typically a flat layer of cells with minimal villous protrusions. The normal synovial villi contain vessels, cells, fluids, electrolytes and proteins. The vessels are small vascular and lymphatic in nature. These structures lining contain angioblasts, the precursor for vascular proliferation. The potential cells contained therein are synovial, red blood, white blood, stem and adipose. The fluids are intravascular and extra-vascular. The fluid contain electrolytes, proteins and various circulating growth factors. Prior to clotting the clear, yellowish fluid portion of blood, lymph, or intramuscular fluid in which cells are suspended is plasma. It differs from serum in that it contains fibrin and other soluble clotting elements. Synovial villa may contain serum, the watery fluid found in tissue edema that accompanies response to injury and disease. If from the tissues of immunized animals, serum contains antibodies and may transfer immunity.

Injured or Responding to Injury or Disease: The altered synovium has prominent and abundant villi. All the ingredients of the normal synovial villi are present in the injured or responding synovium. In addition there may be increased vascularity due to angioblastic proliferation, increased cellularity, increased fluids due to response to injury or disease. There may be increase repair cells, including stem cells at the site. There is typically growth hormones accompanying natural repair process. If there was trauma there may be increase clotting factors and fibrinogen and resultant fibrin mesh for cellular repair or reconstruction. Depending upon the interval following injury and repair there may be fibroblasts or fibrous tissue.

Harvested Synovium: The harvested synovium would have the above components plus the formation of blood clot, fibrin mesh, and eventually over time fibrous or other specific tissue phenotypes; i.e. cartilage, tendon, and bone.

DETAILED DESCRIPTION OF THE INVENTION

All patents, patent applications, government publications, government regulations, and literature references cited in this specification are hereby incorporated herein by reference in their entirety. In case of conflict, the present description, including definitions, will control.

The term "pluripotent" used herein refers to cells which have developmental plasticity and are capable of giving rise to cells derived from any of the three embryonic germ layers, including the mesoderm, endoderm, and ectoderm.

The term "stem cells" used herein refers to undifferentiated cells which are capable of dividing and self-renewal for extended periods, are unspecialized, and can differentiate into many lineages of specialized cell types.

The term "progenitor cells" used herein refers to unspecialized or partially specialized cells which differentiated from stem cells or other cell types and which have the capacity to divide into more than one specialized cell types.

The term "omentum" used herein refers to the fold in the peritoneum which supports the viscera and blood vessels within the abdominal cavity.

The synovium has a plurality of tissue types and cells, all with healing potential. One aspect of this art is to use the explants in total, morcellized, or after in vitro culture to affect the healing of various organs or tissue types. It is known that the synovium or specifically synovial villi are covered with a layer of synovial cells. The synovial cells have pleuripotential healing capacity from primitive fibroblasts to fibrous tissue to cartilage cells. Within the synovium or villi are adipose tissue, blood vessels and lymphatics. There are white blood cells and red blood cells in the vessels. The blood vessels have angioblasts cells for potential healing. The fat contains stem cells. It is known that synovium will regenerate after complete removal. (Key, J. Albert, The reformation of synovial membrane in the knees of rabbits after synovectomy. J. Bone Joint Surg. 7:793. 1925)

The omentum has a plurality of tissue types and cells, all with healing potential. One aspect of this art is to use the explants in total, morcellized, or after in vitro culture to affect the healing of various organs or tissue types. It is known that the omentum is covered with a layer of flat and oval cells. The omentum cells have pleuripotential healing capacity from primitive fibroblasts to fibrous tissue to cartilage cells. Within the omentum are adipose tissue, blood vessels and lymphatics. There are white blood cells and red blood cells in the vessels. The blood vessels have angioblasts cells for potential healing. The fat contains stem cells. It is known that omentum will migrate to areas of disease or injury in the abdomen.

The present invention provides a method of repairing injury to a tissue or an organ in the body of a patient which comprises harvesting of synovium and/or synovial villi from a joint or omentum from the abdomen of a host; taking the cocktail of cells: synovial, red blood, angioblasts, white blood cells, fibroblasts, fat cells, stem cells (optionally placing them in biologically compatible vehicle) for placement in or around the organ or tissue defect. The cocktail of cells can be placed directly into the patient or alternatively into an intermediate medium for culture and/or tissue specification prior to the transplantation or return to the host. In some embodiments the synovial cells or omental cells are separated out with or without other cells for culture and replacement. In further embodiments, the stem cells, pluripotential cells or progenitor cells can be frozen and stored by techniques known in the art to preserve the cells for future thawing and use if needed later in life. In some embodiments of the present invention, the damaged tissue which is treated is mesenchymal, such as bone, cartilage, muscle, ligaments, tendons, and bone marrow. Mesenchymal stem cells are capable of differentiating into various cell types, including at least osteoblasts, chondrocytes, adipocytes, myoblasts, fibroblasts and marrow stroma. Chondrocytes synthesize randomly oriented type II collagen and proteoglycans as their extracellular matrix to thereby form cartilage. Osteoblasts form bone on cross-linked type I collagen in alternately parallel and orthogonal oriented laminae. In some embodiments, the damaged tissue which is treated is non-mesenchymal (i.e. endodermal or ectodermal tissue types). Mesenchymal stem cells can express phenotypic characteristics of be endothelial, neural, smooth muscle, skeletal myoblasts, and cardiac myocyte cells, therefore the present invention can be used to replace these cell types. Some findings indicate that bone marrow stem cells can differentiate into epithelial cells. Therefore, in some embodiments, the damaged tissues include liver, kidney, lung, skin, gastrointestinal tract. Other studies indicate that bone marrow stem cells can differentiate into myocytes. Therefore, in further embodiments the damaged tissues are heart or skeletal muscle. While some embodiments require the cells to be isolated and reintroduced into the damaged tissues, other embodiments encompassed by the present invention rely upon the ability of stem cells which have been mobilized to home in on the damaged tissue. Furthermore, in some embodiments the treatment is allogeneic, that is, the stem cells from or progenitor cells are isolated from a donor patient and are used to treat damaged tissue in a recipient patient. This intra operative method may provide the same potential for harvesting a person's stem cells for future use as does the well known method of saving frozen umbilical cord blood. The shelf life of the frozen cells is known to be at least 15 years.

Synovium constitutes the lining of synovial joints. It consists of series of cells covering lining of fat and vascularity. The cells secrete synovial fluid. These cells naturally shed and can be found in small numbers in synovial fluid. In joint inflammation the lining proliferates into fingerlike projections called villi. These finger like projections are lined with synovial cells and filled with fat and vessels. Therefore there are synovial cells, fat cells with potential for some stem cells, fibroblasts, blood with monocytes and lymphocytes plus angioblasts. The latter are there related to the reaction of the synovium and the increased vascularity. It has been reported by Hunziker and Rosenberg that synovium will grow over cartilage and heal a laceration in cartilage (*J. Bone Joint Surg. Am.* 1996 May; 78(5):721-33).

These villous protrusions of synovium conveniently exist in inflammation and degenerative arthritis and traumatic injuries. Their anatomical nature lends to the capture of the villi by motorized instrumentation during arthroscopy. This tissue if often removed for therapeutic reasons and will reform after approximately six weeks following surgery. (Key, J. Albert, J. Bone Joint Surg. 7:793. 1925) The collection of such tissue can be by various methods. It could then be delivered in variety of ways to injured or disease hyaline or meniscal cartilage. The instrumentation for its harvest exists which is called a synovial resector attachment to the standard motorized instrumentation. The collection devices exist in various forms. The delivery instrument could be as simple as a syringe and needle. The collected material could be delivered in a autogenous fibrin blood clot, via a bioabsorbable sponge, or injected under a patch of autogenous tissue.

The "cocktail" of the multiple tissue types and progenitor cells separated from the synovial villi or omentum tissues have healing potential in articular and meniscal cartilage. The cocktail of cells can include cells such as synovial cells, red blood cells, angioblasts, white blood cells, fibroblasts, fat cells, stem cells and progenitor cells. Originally stem and progenitor cells were harvested by bone marrow biopsy or aspiration. This surgical procedure is often performed within a hospital and has an accompanying morbidity. Mesenchymal stem cells have been harvested from marrow, periosteum and muscle connective tissue. Recently, stem cells have been identified outside of the marrow in a variety of tissues including fatty tissue and in the circulating blood. This discovery lead to the advent of chemical substances such as filgrastim (G-CSF) and AMD3100 that can be injected into the patient and increase the yield of progenitor cells in the peripheral blood. AMD3100 bicyclam compound (AnorMED Inc., Langley, British Columbia, Canada) is a small molecule described in U.S. Patent Application Publication No. 2003/0130250 to Bridger et al. that inhibits stromal cell derived factor-1 (SDF-1) binding to its receptor CXCR4 on CD34+ cells currently in clinical trials. U.S. Provisional Patent Application Ser. No. 60/607,676 to Johnson, hereby incorporated herein by reference in its entirety, describes other methods of mobilizing stem and progenitor cells.

Most hospitals perform leukophoresis, a method of separating out patient cells from blood. For any engraftment procedure, the number or stem and progenitor cells recovered must be known. The number of blood progenitor cells can be measured by the colony forming unit-granulocyte macrophage (CFU-GM) assay, however the assay takes ten to fourteen days to complete, which is too slow for clinical relevance. The CD34 antigen is a useful indicator for measuring the potential for engraftment. CD34 is an adhesion molecule which is expressed on only a few percent of primitive bone marrow cells. The CD34 antigen is associated with human hematopoietic progenitor cells. It is found on immature precursor cells and all hematopoietic colony-forming cells, such as CFU-GM and BFU-E unipotent cells, and CFU-GEMM, CFU-Mix, and CFU-Blast pluripotent progenitors. Fully differentiated hematopoietic cells lack the CD34 antigen. Almost all of the colony-forming unit activity is found in CD34 expressing populations in human bone marrow.

CD34 antigen has been widely used to estimate the number of stem cells in a cell population and to enrich for stem cell populations. The CD34 anitigen is an approximately 110-115 kilodalton monomeric cell surface glycoprotein that is expressed selectively on human hematopoietic progenitor cells. The partial amino acid of a highly purified CD34 antigen has been analyzed, and it was found that it had no significant sequence similarity with any previously described structures. The antigen is not a leukosialin/sialophorin family despite structural similarities, and from a cDNA clone for CD34 from a KG-1 cell library enriched using the anti-CD34 monoclonal antibodies MY10 and BI-3C5 it has been determined to be a sialomucin. Hematopoietic cell lines KG-1, KMT-2, AML-1, RPMI 8402, and MOLT 13 express a 2.7 kilobase CD34 transcript. The cDNA sequence codes for a 40 kilodalton type I integral membrane protein with nine potential N-linked and many potential O-linked glycosylation sites which is a type I transmembrane protein. The 28 kilobase CD34 gene includes eight exons mapped from the coding sequences. The CD34 transcription start site is 258 base pairs upstream of the start site of translation. Anti-CD34 monoclonal antibodies My10 and 8G12, known in the art, bind to two different epitopes of the CD34 antigen expressed on stem cells. Lineage-specific antigens CD71, CD33, CD10, and CD5 are lacking on progenitor cells which are not lineage committed (CD34+ CD38−). The CD34 antigen can be used to estimate stem cell enrichment. It is estimated that a minimum of approximately $2.5 \times 10^6$ CD34$^+$ progenitors per kilogram patient weight are needed for effective hematopoietic reconstitution during bone marrow transplantation procedures.

Populations of stem cells and progenitor cells can be enriched by utilizing surface markers such as c-kit, CD34, and H-2K. Surface markers such as Lin are typically lacking, or expressed at very low levels, in stem cells, so Lin can be a negative selection marker. Cells that are CD34+ Thy1+ lin−. Sca-1 expressing lineage depleted (lin neg). Cell-surface antigens which can be used to positively or negatively select for undifferentiated hematopoietic stem cells include, but are not limited to, CD34+, CD59+, Thy1+, CD38(low/−), C-kit (−/low), lin−. Positive selection of marrow for CD34+ CD33− hematopoietic progenitors, and use of c-kit ligand can be used for ex-vivo expansion of early hematopoietic progenitors.

Stem cells have also been isolated by density-gradient centrifugation from bone marrow aspirates. Mesenchymal stem cells have been shown to adhere to polystyrene while other cells found in bone marrow aspirates, i.e. cells of hematopoietic lineage do not adhere to polystyrene tissue culture materials.

Recently it has been discovered that hematopoietic stem cells, which are derived from mesoderm, can give rise to skeletal muscle, which is derived from mesoderm, and neurons, derived from ectoderm. This capability has been termed "plasticity", "unorthodox differentiation", or "transdifferentiation" in the literature. In one embodiment of the present invention, the stem cells are used to repair or regenerate skeletal muscle. In another embodiment of the present invention the stem cells are used to repair or regenerate neural tissue.

Once the cells have been separated from the synovial or omentum tissue, an aliquot can be taken to grow out so as to identify the cell types in the cocktail by culturing procedures and assays known in the art. Optionally, the separated cells can be analyzed by epitope labelling and flow cytometry. The cells can optionally be frozen and stored by protocols known in the art and described in U.S. Pat. Nos. 5,004,681; 5,192,553; 6,461,645; 6,569,427 and 6,605,275 to Boyse et al. incorporated herein by reference in their entirety. Optionally, prior to harvesting the synovial or omentum tissue or after introducing the separated cells into the damaged tissue, it is encompassed by the present invention that the cells are mobilized by a physical means. Any physical means including, but not limited to lithotripsy, MRI, and CAT can be used as described in co-pending U.S. patent application Ser. No. 11,210,078 to Johnson (Johnson 4.1-5), hereby incorporated herein by reference in its entirety.

It has been postulated that circulating marrow progenitor cells find their way to the local areas of injury for healing influence. The stem cells have the capacity to home in on specific tissues and engraft within the tissue. The process is not thoroughly understood, however various adhesion receptors and ligands which mediate the cell-matrix and cell-cell binding have been studied (Quesenberry and Becker, *Proc. Natl. Acad. Sci. USA*, vol. 95, pp. 15155-15157 (1998)). Some of the adhesion molecules studied include L, P and E selecting, integrins, VCAM-1, ICAM-1, VLA-4, VLA-5, VLA-6, PECAM, and CD44. The cells can therefore be infused via a large-bore central venous catheter, whereupon the stem cells will home in to the tissue in need of repair. Alternatively, the cells can be surgically implanted at a specific site at or near the damaged tissue. Allogenic transplants require careful donor and recipient matching for major histocompatibility (HLA) antigens. In the case of stem cell transplantation for bone marrow reconstitution graft-versus-host disease (GVHD) must be considered.

Clinical applications of the present invention include methods to retrieve cells in any general hospital whereupon the cells will be readily available for transplant for cancers including leukemia, and cartilage and/or bone injury and diseases. Indications for allogeneic stem cell transplants include: acute leukemia, myelodysplastic syndrome, chronic myeloid leukemia, severe aplastic anemia, indolent lymphoma, chronic lymphocytic leukemia, severe immunodeficiency syndromes, and hemoglobinopathies. Indications for autologous stem cell transplantation include: progressive large-cell lymphoma, progressive Hodgkin's disease, multiple myeloma, relapsed germ cell tumors. The present invention can be used to repair or regenerate bone marrow for the treatment of these cancers. In other embodiments the invention can be used to repair or regenerate other tissues, including but not limited to organs, cartilage and bone. Cardiac muscle can by treated as described in U.S. Pat. No. 6,387,369 to Pittenger et al., hereby incorporated herein by reference in its entirety. Connective tissue can by treated as described in U.S. Pat. Nos. 5,197,985; 5,226,914 and 5,811,094 to Caplan et al., hereby incorporated herein by reference in their entirety. Chondrogenesis can be promoted as described in U.S. Pat. No. 5,908,784 to Johnstone et al., hereby incorporated herein by reference in its entirety. The cells can be implanted into the damaged tissue using a matrix such as described in U.S. Pat. No. 6,174,333 to Kadiyala et al. Research is being done on the application of stem cells for a wide array of uses (Eg. Scheffold et al., Purified allogeneic hematopoietic stem cell transplantation prevents autoimmune diabetes and induces tolerance to donor matched islets. *Blood.* 1999; 94 (suppl 1): 664a.; Perry T. E. and Roth S. J., Cardiovascular tissue engineering: constructing living tissue cardiac valves and blood vessels using bone marrow, umbilical cord blood, and peripheral blood cells. *J. Cardiovasc Nurs.* 2003; 18:30-37.)

EXAMPLE 1

Explants from total knee surgery are the host. The first pilot study takes sterile aspirates from patients with degenerative arthritis of the knee and subjects the fluid to centrifugation. The resulting supernatant is examined by smear or cell block for cellularity and the remainder placed in various defects of the explants. This method is an allograft. The preferred method is an autograft, if possible.

EXAMPLE 2

A second pilot study takes synovium from total knee patient. The synovium is placed in a Ringer's lactate bath and the villi are removed using arthroscopic equipment. The collected material is placed in the meniscal and articular cartilage explants. A circular defect in each is the surgical control. The treated explant is filled with the slurry of synovium. If possible, a third hole is filled with the patient's blood and the fourth filled with both the synovial slurry and the patient's blood.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

I claim:

1. A method for treating a patient to repair damaged articular cartilage, which comprises: (a) harvesting of synovial villi from a synovial membrane of a joint of the patient to provide an explant; and (b) introducing the explant into the damaged cartilage, so as to repair the damaged cartilage, wherein the introduced explant comprises synovial villi and all of its harvested components.

2. The method of claim 1, wherein the introduced explant comprises synovial cells, fibroblasts, lymphocytes and angioblasts.

3. The method of claim 1, wherein the introduced explant comprises adipose tissue.

4. The method of claim 1, further comprising the step of culturing the explant in vitro prior to the step of introducing the explant into the damaged tissue.

5. The method of claim 1, further comprising the step of morcellizing the explant prior to the step of introducing the explant into the damaged tissue.

6. A method for treating a patient to repair damaged articular cartilage, comprising:
 a) harvesting a plurality of synovial villi from a joint of the patient;
 b) mincing or morcellizing the collected synovial villi to provide an explant; and
 c) introducing the explant into the damaged articular cartilage, so as to repair the damaged cartilage.

7. The method of claim 6, wherein the introduced explant comprises synovial cells, fibroblasts, lymphocytes and angioblasts.

8. The method of claim 6, wherein the introduced explant comprises adipose tissue.

9. The method of claim 6, further comprising the step of culturing the explant in vitro prior to the step of introducing the explant into the damaged tissue.

* * * * *